United States Patent [19]

Barrut

[11] Patent Number: 5,049,075
[45] Date of Patent: Sep. 17, 1991

[54] DENTURES, AS WELL AS TEMPORARY DENTURES, AND PROCESS FOR THEIR FABRICATION

[75] Inventor: Luc Barrut, Krefeld, Fed. Rep. of Germany

[73] Assignee: Marc Barrut, Lyons, France

[21] Appl. No.: 289,975

[22] Filed: Dec. 23, 1988

[30] Foreign Application Priority Data

Dec. 23, 1987 [DE] Fed. Rep. of Germany ....... 3743674

[51] Int. Cl.$^5$ ............................................. A61C 13/10
[52] U.S. Cl. ..................... 433/196; 433/167; 433/213
[58] Field of Search ............. 433/196, 199.1, 167, 433/171, 214, 191, 264, 213, 190, 193, 194, 195, 181, 182; 264/17, 18; 434/263

[56] References Cited

U.S. PATENT DOCUMENTS

| | | | |
|---|---|---|---|
| 1,089,201 | 3/1914 | Follows | 433/193 |
| 1,270,943 | 7/1918 | Grimm | 433/194 |
| 1,696,422 | 12/1928 | Thayer | 433/196 |
| 2,042,200 | 5/1936 | Torp | 433/213 |
| 2,277,370 | 3/1942 | Sheedy | 433/190 X |
| 2,413,333 | 12/1946 | Myerson | 433/194 X |
| 2,608,760 | 9/1952 | Zahn | 433/171 |
| 2,697,278 | 12/1954 | Kohler | 433/191 |
| 3,104,465 | 9/1963 | Shackelford | 433/194 |
| 3,200,497 | 8/1965 | Goodfriend | 433/214 X |
| 3,787,979 | 1/1974 | Acevedo | 434/263 |
| 4,247,287 | 1/1981 | Gigante | 433/199.1 |
| 4,661,067 | 4/1987 | Harvey, Sr. et al. | 433/181 |
| 4,661,068 | 4/1987 | Harrison et al. | 433/181 |
| 4,758,162 | 7/1988 | Dobbs | 433/191 X |

FOREIGN PATENT DOCUMENTS

| | | | |
|---|---|---|---|
| 530422 | 7/1931 | Fed. Rep. of Germany | 434/263 |
| 631630 | 6/1936 | Fed. Rep. of Germany | 433/213 |
| 2829636 | 2/1980 | Fed. Rep. of Germany | 433/167 |
| 3535266 | 5/1986 | Fed. Rep. of Germany | 433/181 |
| 2122796 | 1/1984 | United Kingdom | 434/263 |
| 8906941 | 8/1989 | World Int. Prop. O. | 433/193 |

Primary Examiner—Robert P. Swiatek
Assistant Examiner—Nicholas D. Lucchesi
Attorney, Agent, or Firm—Remy J. VanOphem

[57] ABSTRACT

For the fabrication of dentures for the upper jaw and/or the lower jaw, a first impression is initially made of the upper jaw and a first impression is made of the lower jaw, a model is prepared for each, and the two are fitted together on an articulator. An individual plate for the upper jaw and/or an individual plate for the lower jaw is prepared on a model and corrected in the oral cavity of the patient. From each corrected individual plate, which is provided with a set of false teeth bondable thereto, temporary dentures are prepared. The row of teeth is shaped and adjusted to each corrected individual plate as a unit and further adjustment of the row of teeth to each corrected individual plae is undertaken while the temporary dentures are being worn. Based on the finally adjusted temporary dentures, a casting mold for the final dentures is prepared and the final dentures are molded.

30 Claims, 13 Drawing Sheets

DENTURES, AS WELL AS TEMPORARY DENTURES, AND PROCESS FOR THEIR FABRICATION

BACKGROUND OF THE INVENTION

The invention pertains to a process for the fabrication of dentures for the upper jaw and/or the lower jaw, in which, with a first impression of the upper jaw and a first impression of the lower jaw, a model of each is prepared, the models are fitted together on an articulator, and an individual plate for the upper jaw and/or an individual plate for the lower jaw is prepared on the models and corrected in the oral cavity of the patient, as well as a process for the fabrication of temporary dentures for the upper jaw and/or the lower jaw and the temporary dentures themselves.

In the sense of the invention, dentures for the upper jaw and/or the lower jaw are understood to be a removable prosthesis for the fully toothless upper jaw and/or lower jaw.

In a known process for the fabrication of dentures for the upper jaw and/or lower jaw, initial impressions are made of the upper jaw and the lower jaw, these impressions are used to make plaster models, and the models are shaped in an articulator. When all of the natural teeth are missing from the upper jaw, an individual plate for the upper jaw is prepared on the model; similarly, when all of the natural teeth are missing from the lower jaw, an individual plate for the lower jaw is prepared on the model; or, when all of the natural teeth are missing from both jaws, both individual plates are prepared.

Using a high-grade impression compound, the individual plates are then fitted exactly to the upper jaw and/or the lower jaw in the mouth of the patient.

A wax wall representing the jaw line and equipped with the false teeth is then applied to the corrected individual plate.

Inside the mouth of the patient, the wax wall with the false teeth is fitted to the individual contours of the patient's mouth, wherein an adjustment to the biting plane represented by any teeth remaining in the lower jaw, or in the reverse case any teeth remaining in the upper jaw, is undertaken.

A different reference plane, e.g., the so-called Frankfurter plane, can also be selected.

Subsequently, based on the corrected plate with the adjusted wax wall and the false teeth, the casting mold for the molding of the dentures for the upper jaw or the lower jaw is prepared and the dentures are molded by casting around the false teeth with a high-grade molding compound.

The simultaneous fabrication of dentures for the upper and the lower jaws is much more complicated. The Frankfurter plane, in which the ideal biting plane is located, is then selected as the reference plane from the beginning. To this end, a physiognomy arch with a bite plate is adjusted to the patient's head; the bite plane will lie in the Frankfurter plane following adjustment. Inside the mouth of the patient, the individual plate for the upper jaw and the individual plate for the lower jaw, both prepared on the models, are also corrected using a high-grade impression compound; the corrected individual plates are provided with a wax wall and false teeth, approximately adjusted to the course of the Frankfurter plane, placed into the mouth of the patient and finally adjusted, whereupon, in keeping with the principle of spot-welding, the two wax walls are joined together at selected points by heating the wax; the unit thus formed is then removed from the patient's mouth, the two wax walls are again separated, the casting molds for the dentures are prepared, and the dentures are molded, to include casting around the false teeth positioned in the casting mold.

Even the fabrication of dentures for the upper jaw only or for the lower jaw only is not without its problems and requires precise work by the treating dentist and painstaking effort on the part of the dental laboratory involved.

With the methods known heretofore, it cannot be absolutely avoided that, following completion of the dentures and during the ensuing normal daily wear and use of same, the wearer will experience discomfort and even great pain in the chewing of solid foods (coarse bread, raw vegetables, etc.). The reason therefor is often due to anomalies of the jaws and the remaining teeth caused by long-term tooth deterioration and deformation of the oral cavity as a result of improper oral hygiene over many years, with which anomalies cannot be adequately dealt using methods heretofore practiced. Emergency resolution in the past has often involved reworking the finished dentures or, in many instances, replacing the bothersome dentures with new ones, whereby all too often only slight improvement was realized.

Such complications are particularly likely when a complete set of dentures for both the upper and the lower jaw must be fabricated for a toothless patient.

These difficulties are largely due to the fact that, in the adjusting and fitting of the individual plates, the latter are placed into the patient's mouth for only a short period of time and the patient must open and close his mouth repeatedly, while wax is carefully removed from or added to the wax walls until, based on the impression or the feeling of the patient at the moment, an optimal fit or adjustment has been presumably attained.

It is readily evident that the patient, during this adjusting and fitting work, can err in his momentary impressions and be convinced that an optimal fit has been reached, which then turns out to be in error during subsequent wearing of the finished dentures.

Furthermore, it is not possible in any of these cases to determine in advance of the fabrication of the dentures whether the future wearer of the dentures will be able to chew solid foods. It is likewise not possible to incorporate in advance assurances that the denture wearer will be able to speak without impediment and with optimal enunciation.

The fabrication methods used heretofore have, moreover, a further critical disadvantage: When dentures must be made for the upper jaw, the lower jaw, or both jaws, it is often necessary to pull any teeth remaining in either or both jaws of the patient. Until the finished dentures can be worn, however, a period of time often lasting for several weeks lapses, which period of time is primarily dependent upon the time required for the gums to heal. During this time, the patient wears a clip on the toothless jaws with blinders to mask the absence of the front teeth. During this time, however, the patient can neither speak distinctly nor eat solid food.

SUMMARY OF THE INVENTION

Fundamental to the invention is an objective of establishing a process, whereby dentures are fabricated for the upper jaw and/or the lower jaw, in which, with a first impression of the upper jaw and a first impression of the lower jaw, a model of each is prepared, the models are fitted together on an articulator, and an individual plate for the upper jaw and/or an individual plate for the lower jaw is prepared and corrected in the oral cavity of the patient.

Equally basic to the invention is an objective of establishing a process for the fabrication of temporary dentures for the upper jaw and/or the lower jaw, in which, with a first impression of the upper jaw and a first impression of the lower jaw, a model of each is prepared, the models are fitted together in an articulator, and an individual plate for the upper jaw and/or an individual plate for the lower jaw is prepared and corrected in the oral cavity of the patient.

Also fundamental to the invention is an objective of creating temporary dentures for the upper jaw and/or the lower jaw.

In keeping with the invention, the first objective is realized according to a first resolution principle, in that temporary dentures are prepared from each corrected plate and a row of false teeth bondable thereto, the row of teeth is designed to be adjustable as a unit to the corrected individual plate. Further adjustment of the row of teeth to the corrected individual plate is undertaken while the temporary dentures are being worn, and, based on the finally adjusted temporary dentures, the casting mold for the final dentures is prepared and the final dentures are molded.

In complete departure from the current state of the art, the corrected individual plates are not coated with wax, equipped with false teeth, then corrected inside the mouth of the patient in such a short period of time that he is unable to develop adequate feel for proper fit and bite. Rather, the corrected individual plates with the rows of false teeth themselves form the temporary dentures, which are adjustable within the mouth of the patient, while the natural teeth of the lower jaw, in the case of dentures for the upper jaw, and the natural teeth of the upper jaw, in the case of dentures for the lower jaw, define the chewing plane, by their biting surface to which the row of teeth is adjusted.

In complete departure from the fitting and adjusting procedures used heretofore, the process of the invention provides that, after the insertion of temporary dentures, the row of teeth is so adjusted that the patient experiences comfortable wear. After a few days, or even sooner, the row of teeth is, when necessary and as often as required, readjusted until the patient has the feeling that he is again eating and speaking with his natural teeth.

The special advantage lies in the fact that temporary dentures, following adjustment for match and fit, fully agree with the final dentures, i.e., the wearing characteristics of the two are identical, and the patient, once the temporary dentures are properly fitted, i.e., have been properly adjusted, will notice no difference with the final dentures.

An additional significant advantage is represented by the fact that the patient, until the final dentures are finished, can in every respect move freely, naturally, unimpededly, and in full confidence in his environment while wearing the temporary dentures.

As soon as the temporary dentures are properly seated, an impression is made to prepare the casting mold for the final dentures, the mold is prepared, the false teeth patterned on the row of teeth are positioned in the mold, and the final dentures are molded by casting around the positioned false teeth. Following the making of the impression, the patient can continue to wear the temporary dentures until the final dentures are ready.

Yet another significant advantage lies in the fact that, with temporary dentures for the upper jaw and the lower jaw, correction of anomalies can be undertaken in such a way that the two rows of teeth can also be adjusted to a reference plane, e.g., the so-called Frankfurter plane.

The second objective is also realized in keeping with a first resolution principle in that temporary dentures are prepared from each corrected individual plate and a row of false teeth bondable thereto, wherein the row of teeth is fitted to the corrected individual plate as a unit.

The first objective can also be realized in keeping with a second resolution principle in that a physiognomy arch with a row of false teeth matched to the upper jaw and/or the lower jaw is placed on the patient's head, the row of teeth is adjusted to a reference plane, while maintaining this alignment the row of teeth is shaped in the articulator, an individual plate for the upper jaw and/or the lower jaw is prepared on the models and corrected in the oral cavity of the patient, the row of teeth is adjustably bonded to the corrected individual plate, further adjustment is undertaken while the patient is wearing the temporary dentures, and, based on the adjusted temporary dentures, the casting mold for the dentures is prepared and the dentures are molded.

By virtue of these measures, precision in the fabrication of the temporary dentures in keeping with the invention is enhanced even further. In particular, anomalies or defomities of the upper jaw and/or the lower jaw can be better corrected than in the resolution principle, since the rows of teeth are adjusted in the patient's mouth and the individual plates for these rows of teeth are optimized on the models and further corrected in the patient's mouth. Adjustment work is greatly simplified thereby.

In another modification of the second resolution principle, the impression plate is affixed to a physiognomy arch and adjusted to the reference plane for the preparation of the first impression.

These measures contribute to further simplification of the task of aligning and adjusting the dentures to a reference plane.

The second objective is also realized in keeping with a second resolution principle in that a physiognomy arch with a row of connected false teeth matched to the upper jaw and/or the lower jaw is placed on the patient's head, the row of teeth is adjusted to a reference plane, while maintaining this alignment the adjusted row of teeth is shaped in the articulator, and an individual plate for the upper jaw and/or an individual plate for the lower jaw is prepared on the models and corrected in the patient's mouth, and temporary dentures are prepared from each corrected individual plate and a row of connected false teeth bondable thereto, wherein the row of teeth is adjustably fitted to the individual plate as a unit.

In a further modification of the invention, the impression plate is affixed to the physiognomy arch and adjusted to a reference plane.

The process of the invention in keeping with the second resolution principle for the fabrication of dentures for the upper jaw and/or the lower jaw is also used in cases in which the dentures are anchored with implants.

The process of the invention for the fabrication of implant-anchored dentures for the upper jaw and/or the lower jaw, in which a first impression of the upper jaw and a first impression of the lower jaw are used to prepare a model of each, which models are then adjusted in an articulator, is characterized by the fact that a physiognomy arch with a row of false teeth matched to the upper jaw and/or the lower jaw is placed on the patient's head, the row of teeth is adjusted to a reference plane, and, while maintaining this alignment, the adjusted row of teeth is shaped in the articulator, reworked on the jaw line of the model for better fit, inserted into the patient's mouth, and anchored.

In a further modification of the invention, the impression plate is also affixed to the physiognomy arch and adjusted to the reference plane.

The third objective is realized by way of a corrected individual plate for the upper jaw and/or a corrected individual plate for the lower jaw and a row of false teeth bondable thereto.

In keeping with the invention, the row of false teeth is adjustable to the corrected individual plate as a unit.

Also in keeping with the invention, adjusting elements are provided between the jaw cast of each corrected individual plate and the row of teeth, while such adjusting elements are nonpositively and/or positively engaged with the individual plate and the row of teeth.

A given row of false teeth forms, during the adjusting and fitting, a functional unit, i.e., it is adjusted to the corrected individual plate as an entity.

In a first embodiment example, the row of teeth consists of a prefabricated strip of plastic material with imprinted teeth.

For the dental practice, it is sufficient that an assortment of several groups of prefabricated strips of variable lengths are available, which can then be ground or cut to the appropriate height for the individual patients.

In another embodiment of the invention, a tooth-row strip consists of three sections hinged together so that an optimal fit to the outer contour of the temporary dentures is possible.

In a further embodiment, the false teeth are fitted onto a profiled track, which track is engaged with centering elements.

In yet another configuration of the dentures of the invention, each jaw cast of the individual plate is provided with a displaceable and arrestable profile for the adjusting elements. By this provision, it is possible with the centering element, during the adjustment of the temporary dentures, to adjust the entire row of teeth toward or away from the lips.

A further embodiment form of the invention provides that the profile and each individual plate are joined together in keeping with the dovetailing principle, so that a simple shifting union is created, which advantageously has a frictional adhesion level so high that clamping screws, etc., are not needed for arresting.

For the mutual arresting or anchoring of each individual plate and the row of teeth, a first embodiment example of the invention has flushly aligned bores with inside threading in both the individual plate and the row of teeth or the profile for the row of teeth, while the adjusting elements are threaded bolts, each of which has two counter-threaded spindle sections and a cross-sectionally prismatic shaft connecting the two spindle sections.

For mutual arresting or anchoring of each individual plate and the row of teeth, a second embodiment example of the invention has adjusting elements, each of which has a cross-sectionally prismatic shaft uniting two spindle-like end sections designed in keeping with the principle of a grub screw, which sections are counter-threaded, while the adjusting elements, using these spindle sections, are threaded into the individual plate and the row of teeth or the profile. These measures make it possible to shift the relative positions of the individual plate and row of teeth prior to their securing with the adjusting elements.

In keeping with still another embodiment form, each adjusting element of the invention consists of two threaded spindles and a sleeve with inside threading, while one end section of each spindle engages in the sleeve and the other end section fits rotatably and positively in an abutment. By way of adequately developed self-inhibition of the threaded spindles, assurance is given that any adjustment made will be retained.

Further refinement of the foregoing characteristic of the invention provides that the abutments are molded in the material of the row of teeth and/or the individual plate. This measure ensures optimal positioning of the adjusting elements during the fabrication of temporary dentures.

In yet another design in keeping with the invention, the other end section of the threaded spindle—the end section not engaged with the sleeve—has the form of a spherical head and the abutment is designed as a ball socket in which the spherical head is rotatably and pivotably mounted with great frictional resistance.

Using these measures, the threaded spindles are enabled to execute, in a simple manner, both adjustment for height and a displacement of the row of teeth in relation to the individual plate.

In yet another configuration in keeping with the invention, each row of teeth to be placed into the physiognomy arch and shaped in the articulator is equipped with a traction bolt.

Further advantageous refinements and designs of the invention, as well as additional embodiment examples, will become apparent when taken in connection with the description of the appended figures.

DETAILED DESCRIPTION OF THE PREFERRED EMBODIMENT

Figure 1:
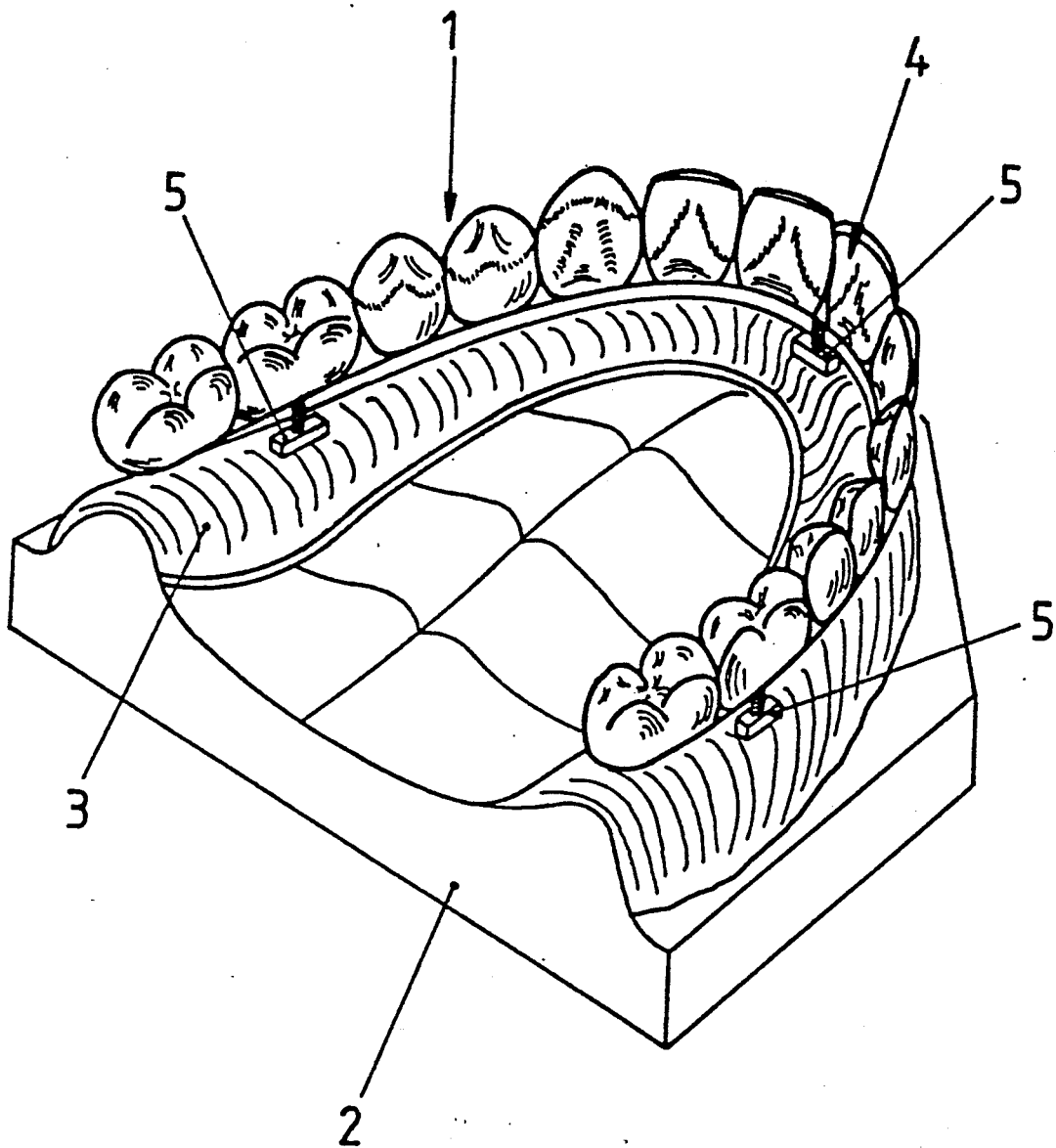
FIG. 1 is a perspective view of temporary dentures for a lower jaw.

In the drawings, identical parts are marked with identical reference symbols.

All of the statements in the ensuing description apply equally to the fabrication of dentures and temporary dentures for both the upper jaw and the lower jaw.

FIG. 1 depicts, in perspective, temporary dentures 1 for the lower jaw, which is surmounted on the model 2 of the lower jaw. The model of the lower jaw is mounted in an articulator, which is not illustrated. The model of the upper jaw similarly mounted in the articulator is also not illustrated.

For the fabrication of dentures, a first impression of the lower jaw is used to prepare the model 2 and a first impression of the upper jaw is used to prepare the unillustrated model of the upper jaw, which two models are then positioned in an articulator and fitted together.

For a toothless lower jaw, an individual plate is prepared on the model, adjusted in the patient's mouth, and fitted in the articulator with an adjustable row of false teeth, which together form an adjustable unit and the temporary dentures. A corrected individual plate 3 with an adjustable row of teeth 4 fitted thereto are illustrated in FIG. 1. For subsequent adjustments, adjusting elements 5 are utilized, which are described in greater detail below and are shown schematically in FIG. 1.

Figure 2:
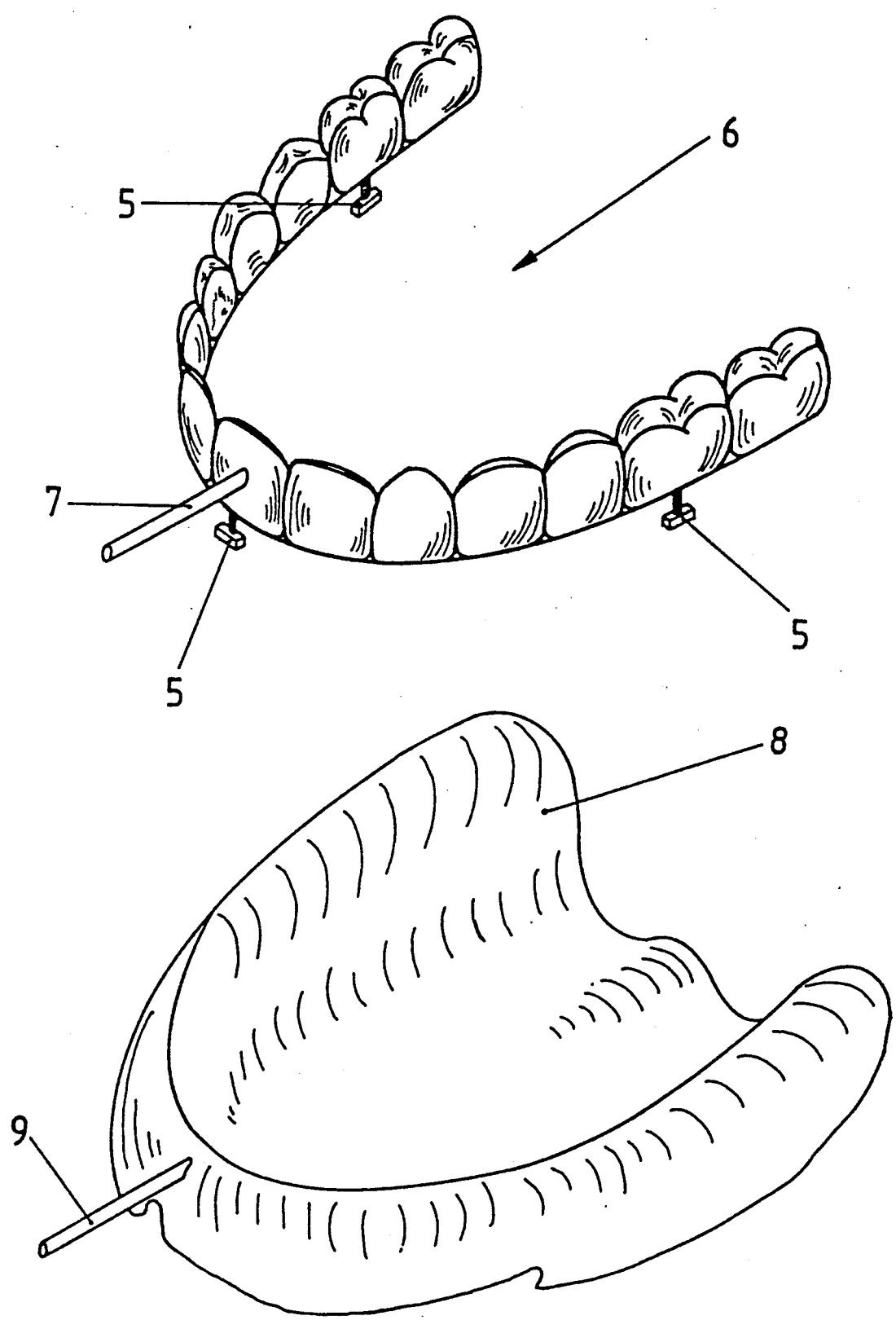
FIG. 2 is a perspective view of a row of teeth and a corrected individual plate for an upper jaw, each equipped with a traction bolt.

Depicted in perspective in FIG. 2 is a row of false teeth 6, which is provided with a traction bolt 7, and an individual plate 8 for the upper jaw, which is similarly equipped with a traction bolt 9. The row of teeth and the corrected individual plate are fastened in a physiognomy arch by their traction bolts, which arch is then placed on the patient's head. By appropriate pivoting and arresting, the row of teeth and the corrected individual plate are adjusted in the patient's mouth and to each other, whereupon they are then positioned in the articulator and adjustably fitted together by the adjusting elements 5.

Figure 3:
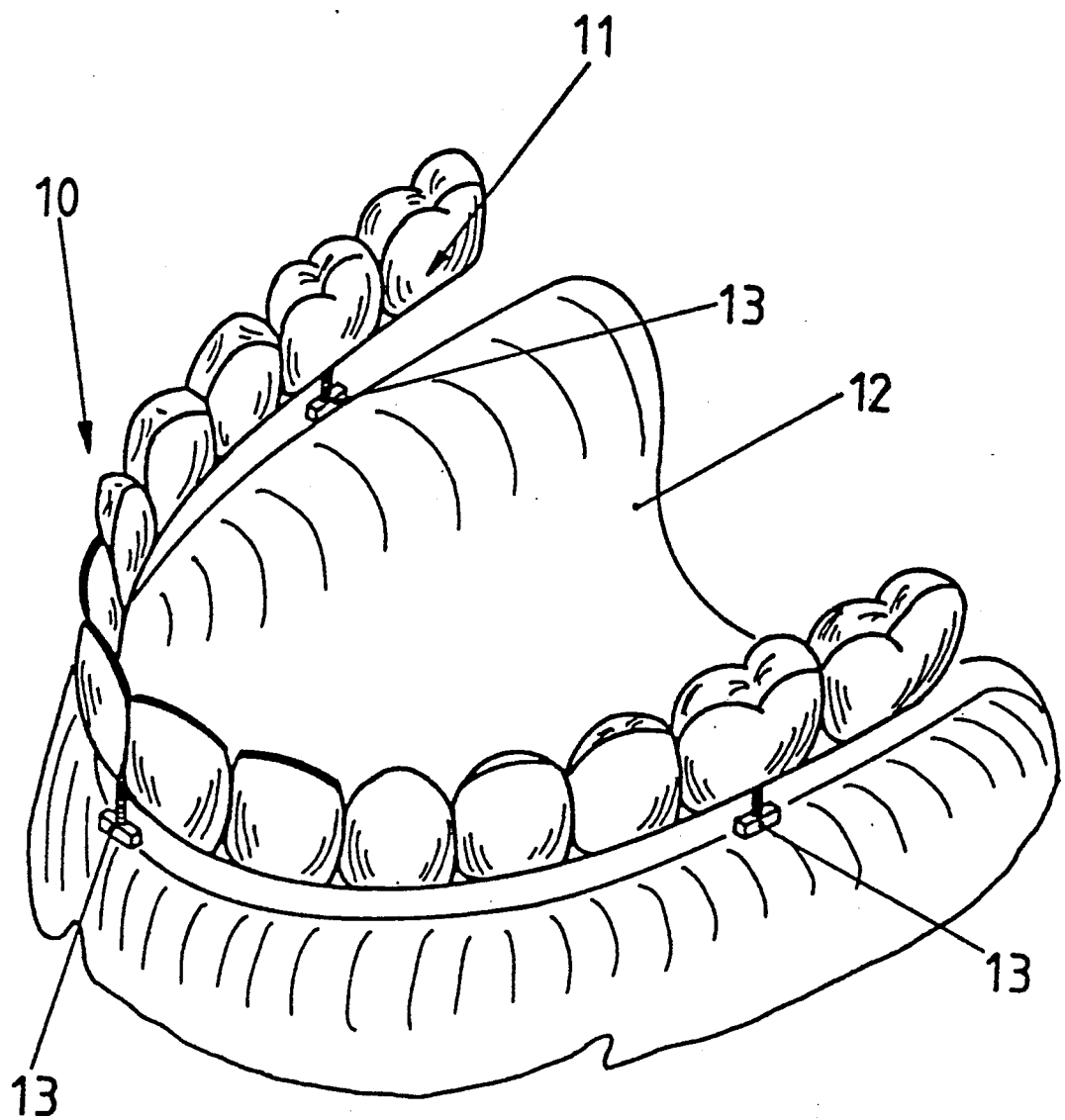
FIG. 3 is a perspective view of temporary dentures for an upper jaw.

FIG. 3 shows, in perspective, temporary dentures 10 for the upper jaw with a row of false teeth 11 and a corrected individual plate 12, which are adjustably fitted together by adjusting elements 13.

In each case of the dentures depicted in FIGS. 1–3, there are three adjusting elements provided between the corrected individual plate and the row of teeth, which elements are used to adjust the positioning of the row of teeth in relation to the individual plate.

This adjustment occurs inside the mouth of the patient, who will then wear the temporary dentures for at least a few days. After optimal adjustment, the temporary dentures are used to prepare the casting mold for the final dentures and the latter are molded.

It is also possible to position a row of teeth as a unit, as shown in FIG. 2, in a physiognomy arch, which is then placed on the patient's head.

The row of teeth is then adjusted to a reference plane, e.g., the so-called Frankfurter plane, and, while maintaining this alignment, the adjusted row of teeth is positioned on the model in the articulator and fitted to an individual plate for the lower jaw and corrected in the mouth of the patient.

The corrected individual plate and the adjustable row of false teeth thus joined together then similarly form the temporary dentures, which are used to mold the final dentures for the lower jaw.

In this case, as depicted in FIG. 2, the row of false teeth 6 includes the traction bolt 7. Through the use of a traction bolt, the row of teeth is positioned in the physiognomy arch, then in the articulator.

Following preparation of the temporary dentures, the traction bolt 7 is cut off. The same holds true for the traction bolt 9.

As illustrated in FIGS. 1–3, the rows of false teeth consist of prefabricated and heat-malleable, e.g., curable with ultraviolet light, strips of plastic material with imprinted false teeth. The strip, after being heated, is appropriately adjusted to the conditions prevailing inside the patient's mouth, then ground or cut to the indicated height. A plastic material curable via polymerization can also be used.

Figure 4:
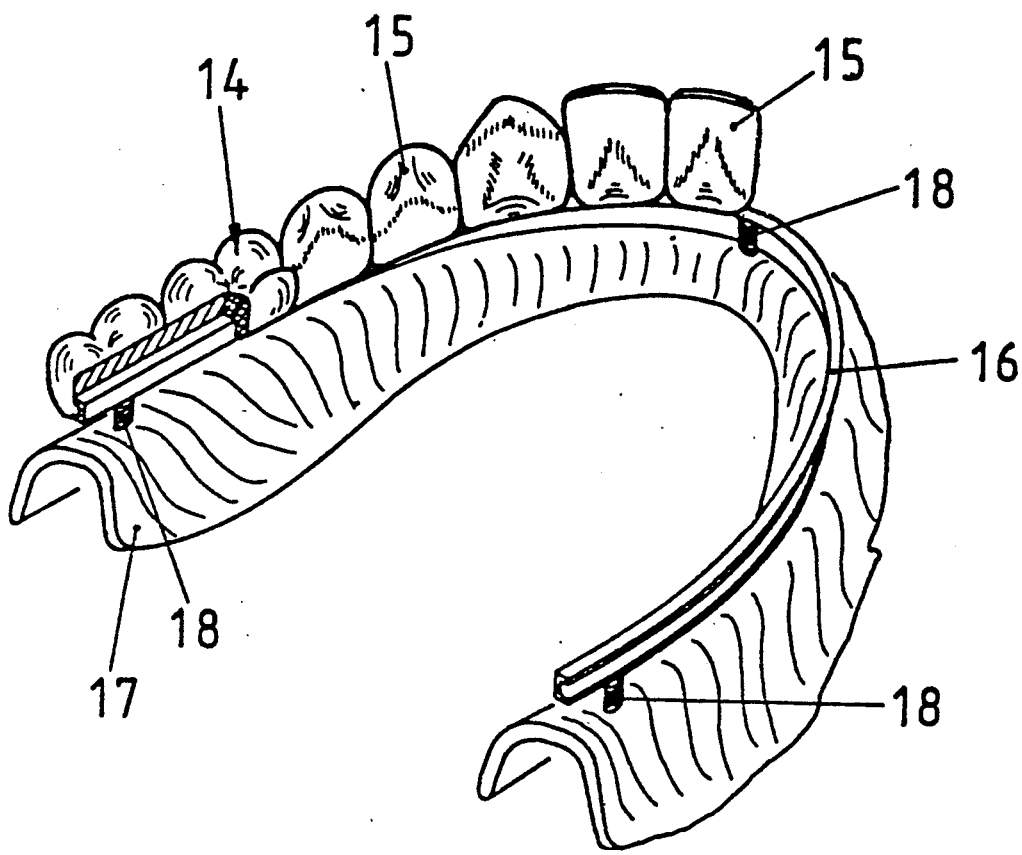
FIG. 4 is a perspective view of an embodiment example of a row of teeth utilized with a profiled track.

FIG. 4 depicts, in perspective and in a modification of the embodiment shown in FIG. 1, a further embodiment of temporary dentures for the lower jaw. The temporary dentures are partially illustrated in cross section.

A row of false teeth 14 consists of individual false teeth 15, which are mounted onto a profiled track 16 to form a positive union therewith. When the individual teeth are pushed into the track under high frictional resistance, it is not necessary to provide an additional arresting means to fix the teeth in place.

Adjusting elements 18 are located between the profiled track and a corrected individual plate 17.

Figure 5A:
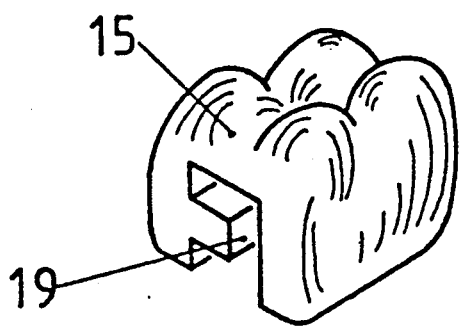
FIGS. 5A and 5B are perspective views of teeth for use with a profiled track.

Shown in perspective in FIG. 5A is a tooth 15 with a groove 19 complementarily matching the profiled track 16, which groove engages both nonpositively and positively in the profiled track acting as a spring.

Figure 5B:
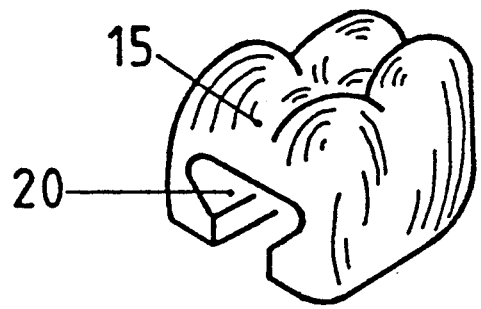

In the same perspective as FIG. 5A, FIG. 5B depicts another embodiment of the positive union between the teeth of the row of teeth and an unillustrated profiled track, in which the nonpositive and positive joining of the two is based on the principle of a dovetailed union. A groove 20 is designed to complement the unillustrated profiled track.

Figure 6A:
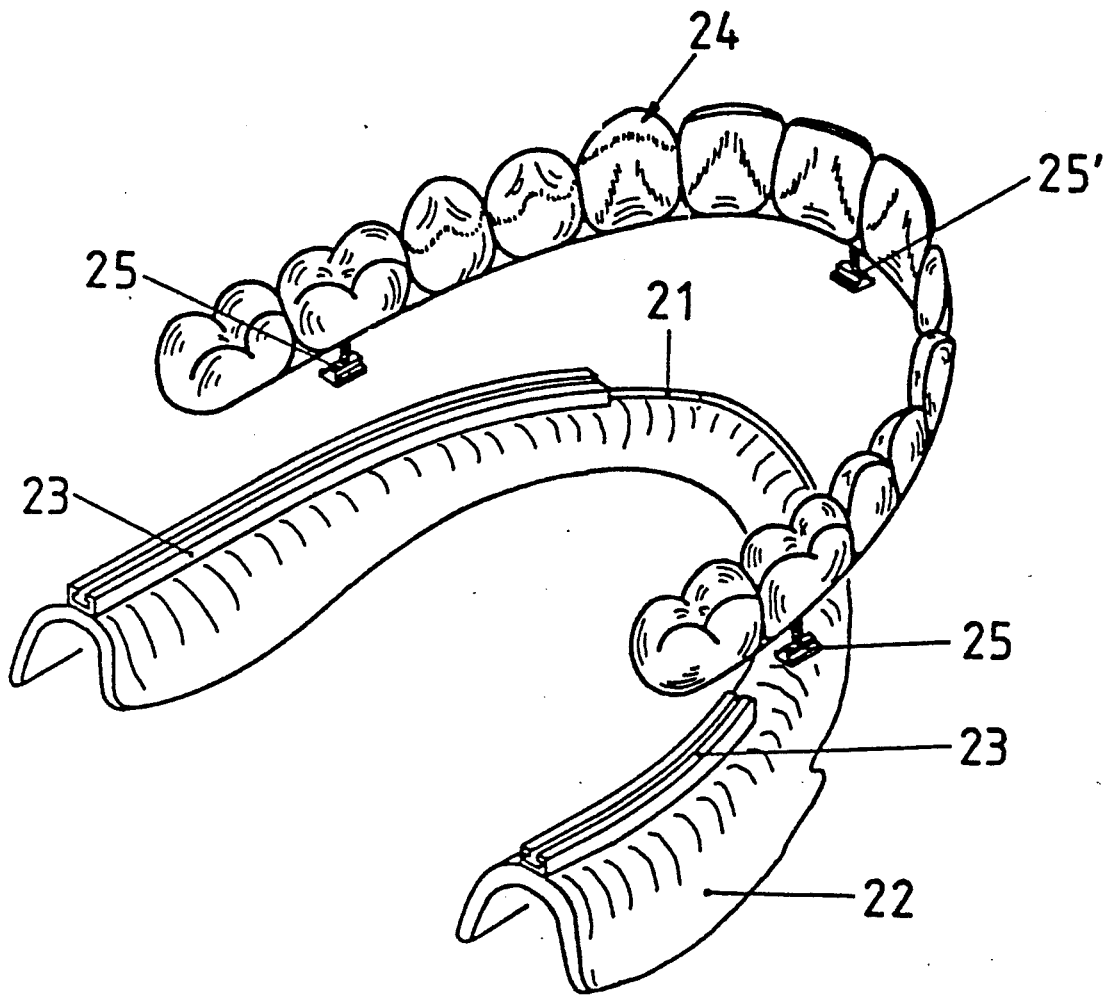
FIG. 6A is a perspective view of an alternate embodiment of a row of teeth utilized with a profiled track.
Figure 6B:
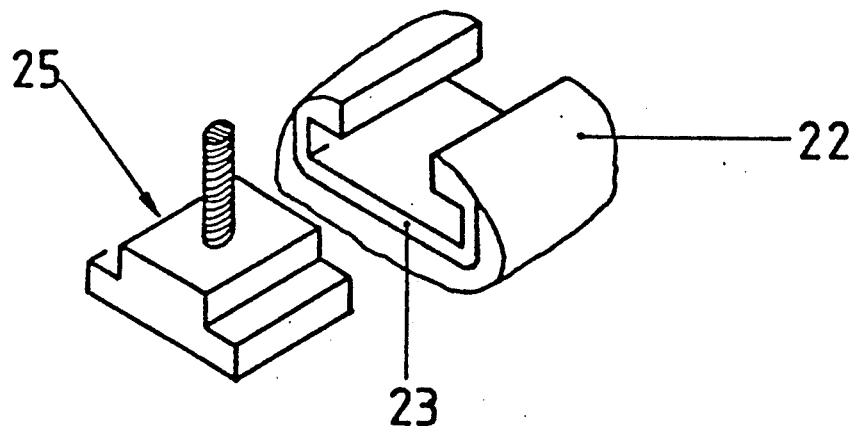
FIG. 6B is a view of a portion of the profiled track and an adjusting element illustrated in FIG. 6A at an enlarged scale.

As depicted in FIG. 6A, which essentially corresponds to FIG. 4, a jaw line 21 of a corrected individual plate 22 is provided with two profile tracks 23 for receiving adjusting elements 25 affixed to the underside of a row of false teeth 24. As illustrated in FIG. 6B, which depicts one of the profiles in an enlarged cutout, the profile tracks are open C-profiles paralleling the row of teeth, in which the two adjusting elements for the area of the jaw teeth are displaceably and arrestably guided, while a third adjusting element 25' for the area of the front teeth is not secured to the row of teeth consisting of a strip of plastic material and to the corrected individual plate until the other two adjusting elements have been fixed or arrested following their adjustment.

FIG. 6B depicts a portion of the individual plate 22 shown in FIG. 6A in which the profiled track 23 is a T-shaped groove which receives the displaceable and arrestable adjusting element (25).

Figure 7:
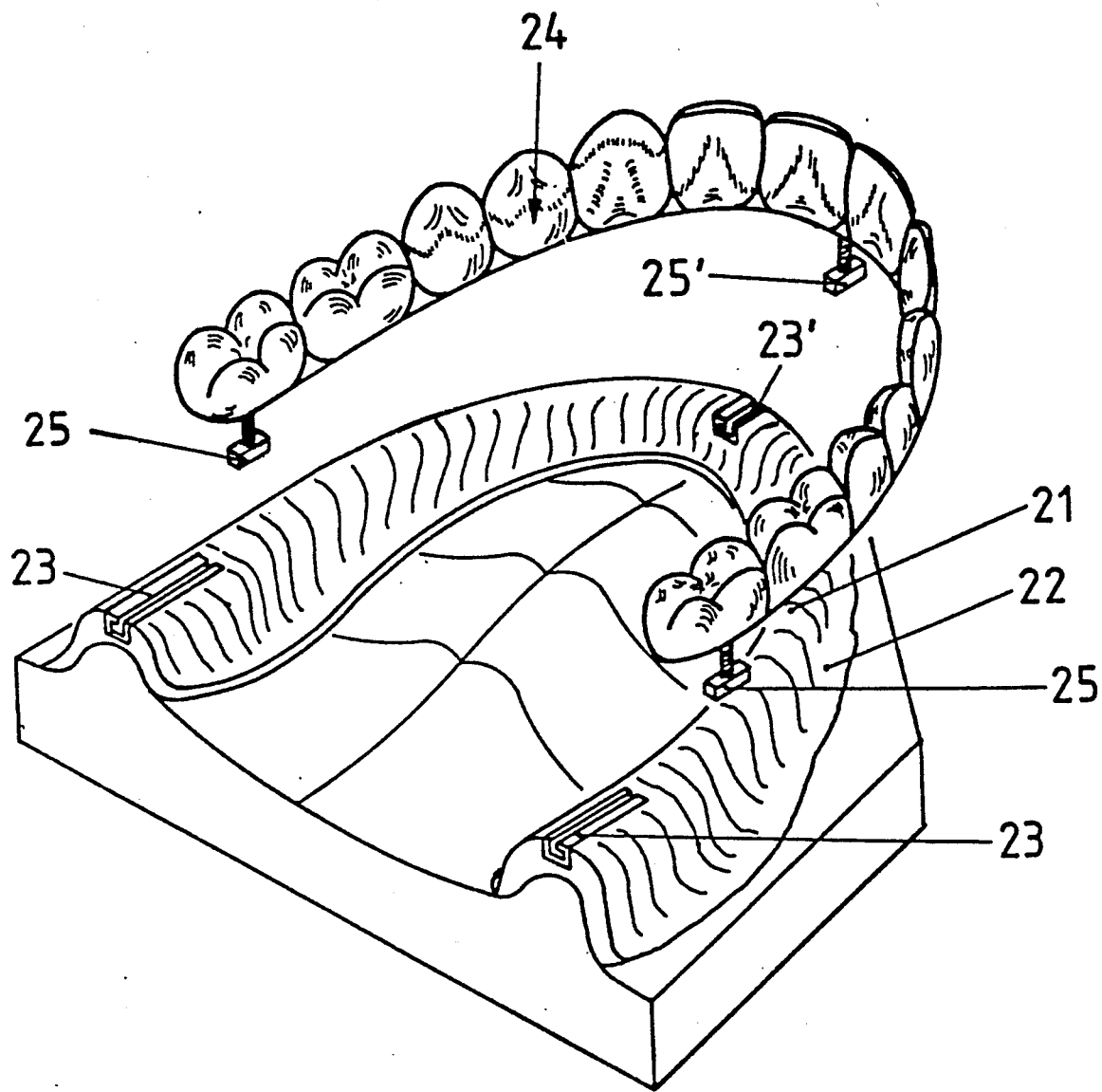
FIG. 7 is a perspective view of another embodiment of temporary dentures for a lower jaw.

In FIG. 7, which essentially corresponds to FIG. 6A, the jaw line 21 of the corrected individual plate 22 also bears the two profile tracks 23 for receiving the adjusting elements 25 affixed to the underside of the row of false teeth 24. As in the case of the design shown in FIG. 6B, the profiles are open C-profiles paralleling the row of teeth, in which the two adjusting elements for the area of the jaw teeth are displaceably and arrestably guided. A separate profile 23' is provided for the third adjusting element 25' for the area of the front teeth, so that the entire row of teeth can be shifted and arrested as a unit in relation to the corrected individual plate. Adjustment of the mutual separation between the row of teeth and the corrected individual plate is then subsequently undertaken.

Figure 8:
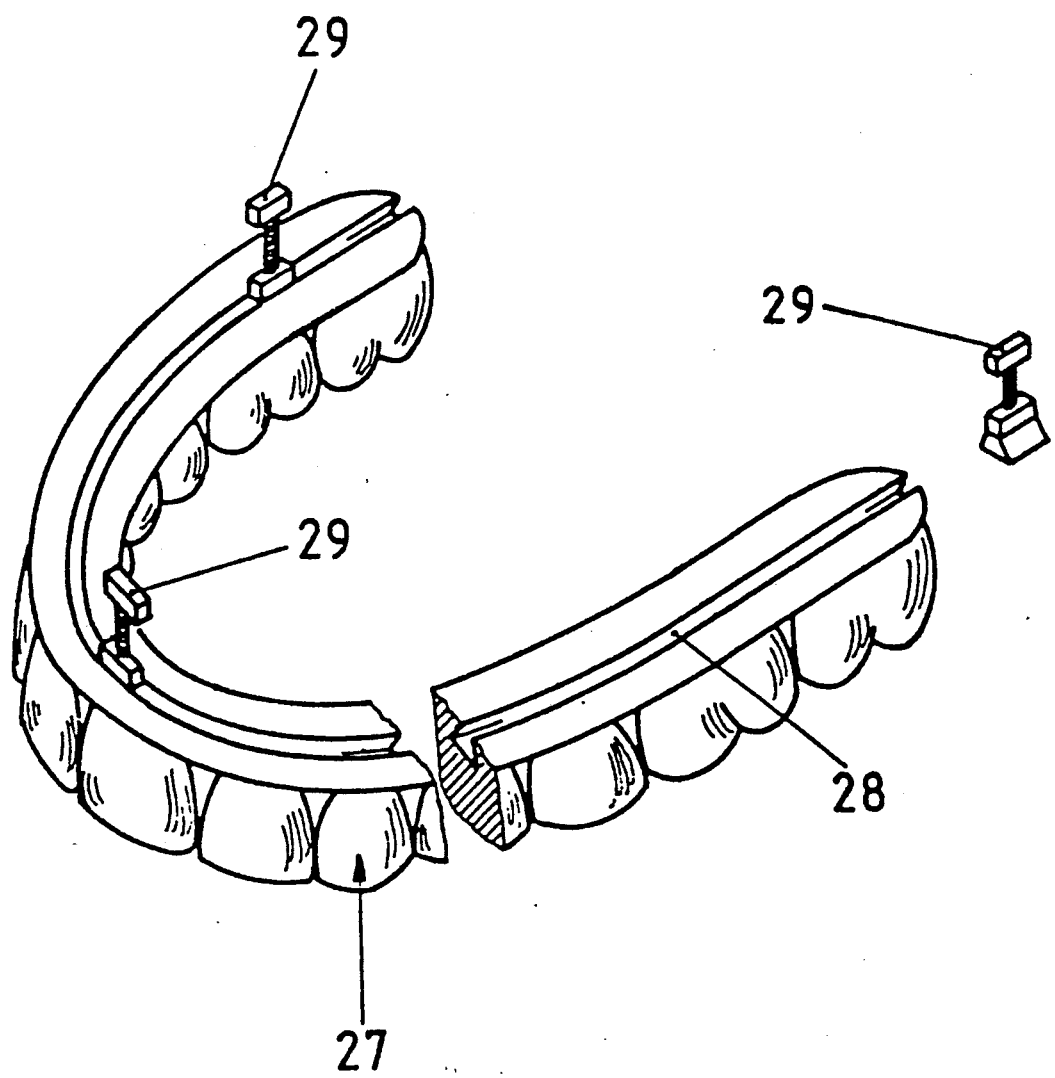
FIG. 8 is a view of a further alternate embodiment of profiled tracks.

FIG. 8 shows, in a modification of the design in FIG. 6A, a row of false teeth 27 with a profile track 28, comparable to the profile tracks in FIG. 6A, on its underside, in which displaceable adjusting elements 29 are guided.

When the adjusting elements are fitted into the grooves under high frictional resistance, it is not necessary to provide an additional arresting means to fix the false teeth in position as a unit.

It is, therefore, possible, during the course of the fitting of the temporary dentures, to displace the entire row of teeth, using the adjusting elements, toward or away from the lips in the sense of an adjustment.

Figure 9:
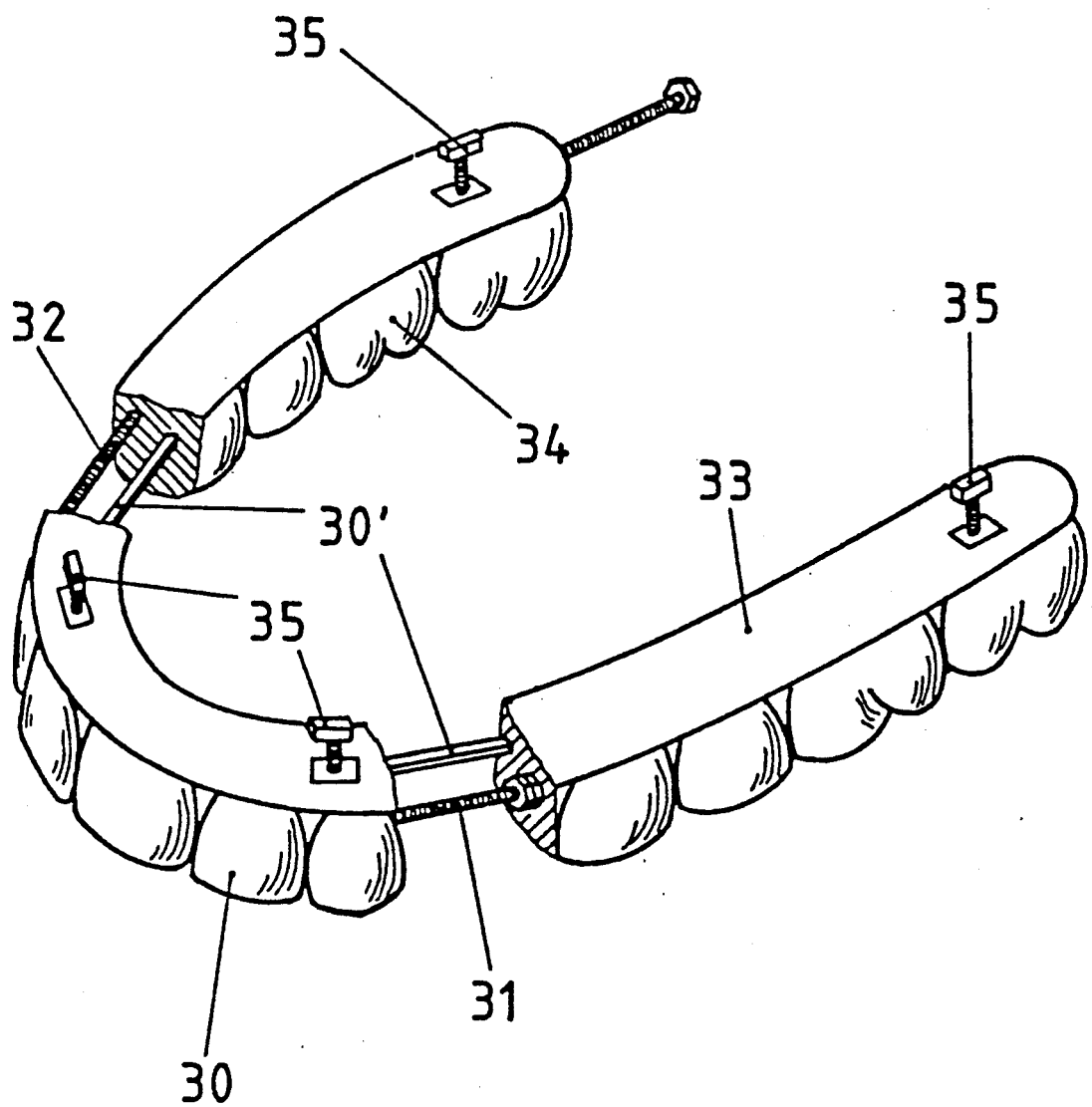
FIG. 9 is a view illustrating a row of teeth with a flexible spindle.

FIG. 9 depicts another embodiment of a row of flase teeth. The row of false teeth has a front-teeth segment 30 with two flexible threaded spindles 31 and 32 rotatably mounted between the front-teeth segment and premolar-molar segments 33 and 34 which are forcibly guided on tracks 30'. By rotating the two threaded spindles, the separation of the premolar-molar segments 33 and 34 from the front-teeth segment can be adjusted. Each of the front-teeth and premolar segments include adjusting elements 35 on their underside, by which the adjustable and height-variable union with the unillustrated corrected individual plate is established.

Figure 10A:
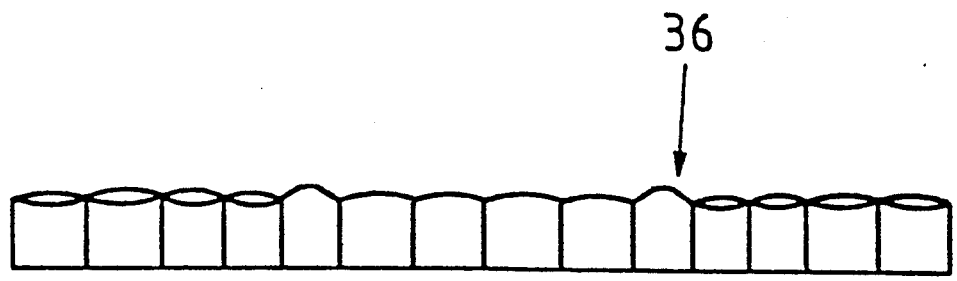
FIGS. 10A and 10B illustrate examples of a strip of material with imprinted teeth.

Shown in FIG. 10A is a strip of plastic material 36 with imprinted teeth. In a dental practice, the plastic material 36 is available in a selection of several groups of prefabricated strips of different lengths which can be ground to the appropriate length and height for the individual patients.

Figure 10B:
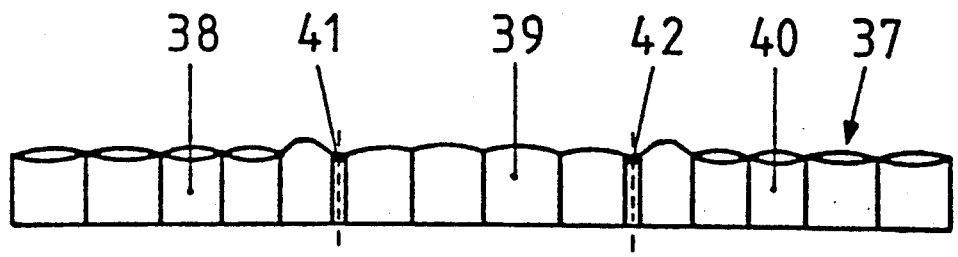

The strip of plastic material 37 with imprinted teeth shown in FIG. 10B is composed of three articulated sections 38, 39, and 40 which are joined together by hinges 41 and 42, so that optimal fitting to the outer contour of the temporary dentures is possible.

Figure 11:
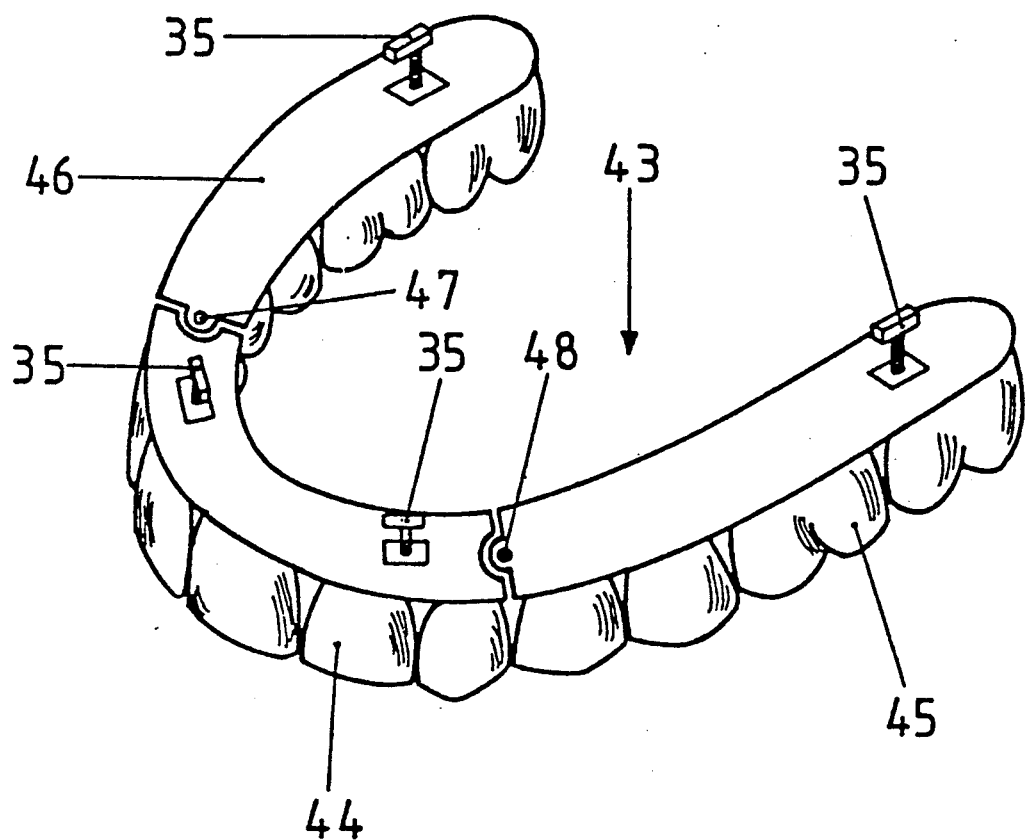
FIG. 11 is a perspective view of a first embodiment of a row of teeth with hinged sections.

Depicted in FIG. 11 is a row of false teeth 43 having three articulated sections 44, 45, and 46. The union established by two hinges 47 and 48 is such that the articulated sections can be pivoted only in a plane perpendicular to the axes of the hinges.

Figure 12:
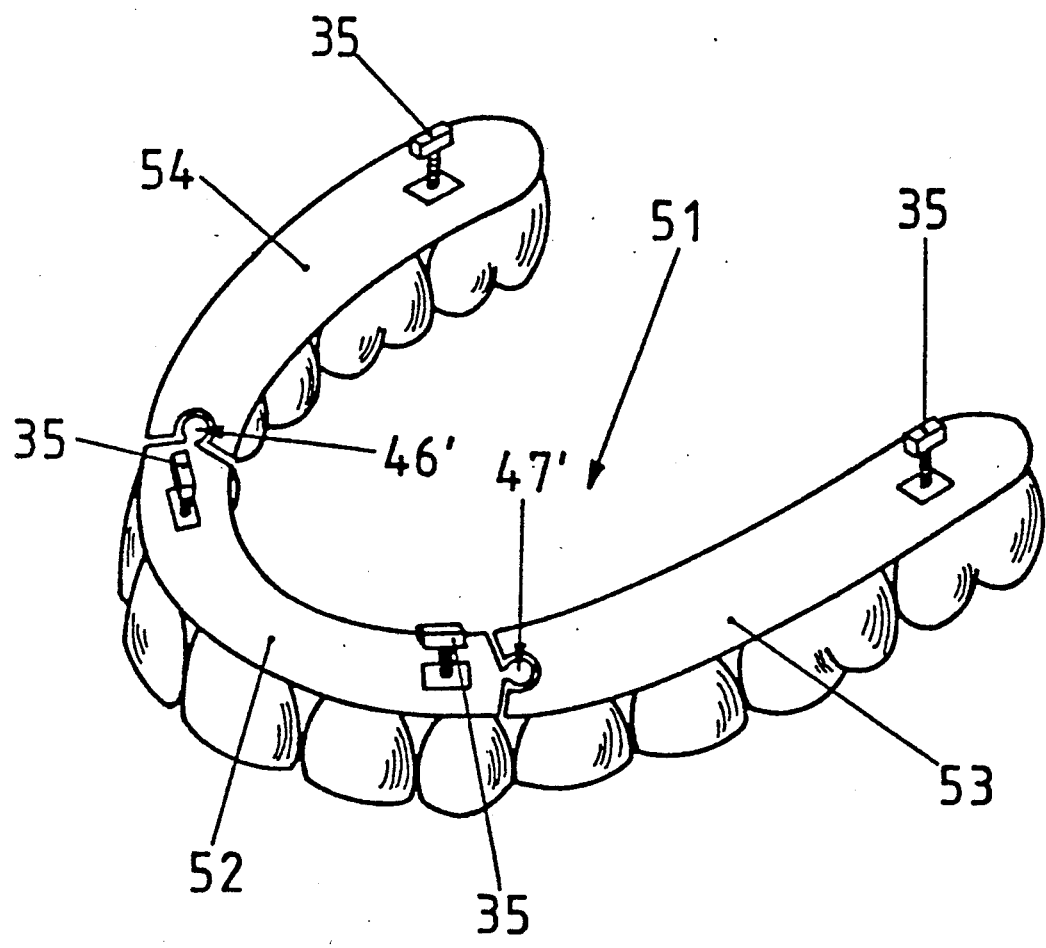
FIG. 12 is a perspective view of a second embodiment of a row of teeth with hinged sections.

A similar row of false teeth 51 is illustrated in FIG. 12 which has three articulated section 52, 53, and 54. However, joining of the articulated sections (as shown at 46', 47') is accomplished with a ball-and-socket joint, so that the sections can be adjusted, not only in the plane described for the sections shown in FIG. 11, but also in any desired direction.

In the simplest case, e.g., in the embodiment shown in FIGS. 1 and 3, the mutual arresting and anchoring of the individual plates and the rows of teeth is achieved by way of counter-threaded, flushly aligning bores in both the individual plates and the rows of teeth or the profile tracks thereon, while the adjusting elements take the form of threaded bolts.

Figure 13:
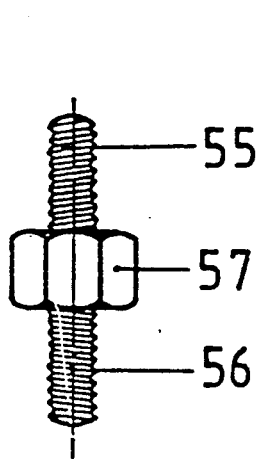
FIGS. 13–18C illustrate various examples of the adjusting elements.

The adjusting elements are illustrated in FIG. 13. They have two spindle sections 55 and 56 with counter-threading, which are joined together by a cross-sectionally prismatic shaft 57.

Figure 14:
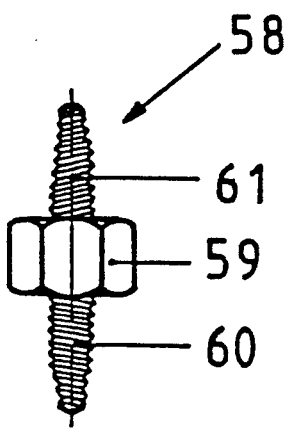

FIG. 14 depicts another embodiment of an adjusting element 58. The adjusting element 58 also has a cross-sectionally prismatic shaft 59 uniting two spindle sections 60 and 61 designed in keeping with the principle of a grub screw. In this case, it is not necessary that the row of teeth or its profile track and the corrected individual plate have bores, since these adjusting elements can, when suitable material has been selected, readily self-thread themselves into any point on the row of teeth or its profile track and on the corrected individual plate.

In both cases, the spindle sections are counter-threaded, while their tightening into the adjusting elements in the row of teeth or its profile track and the corrected individual plate is accomplished with a spanner applied to the prismatic shaft.

This also applies to the embodiments described below and illustrated in FIGS. 15 and 16.

Figure 15:
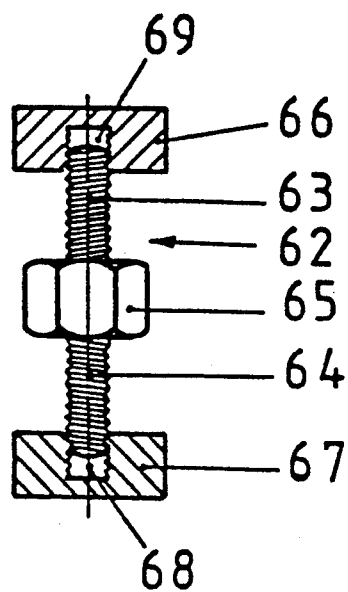

An adjusting element 62 as depicted in FIG. 15 has two counter-threaded spindles 63 and 64 and a cross-sectionally prismatic shaft 65 connecting them. The free end sections of the threaded spindles are rotatably mounted in abutments 66 and 67, which have blind bores 69 and 68, respectively, with internal threading. The abutments are cemented or cast in the row of teeth or its profile track and in the corrected individual plate.

Figure 16:
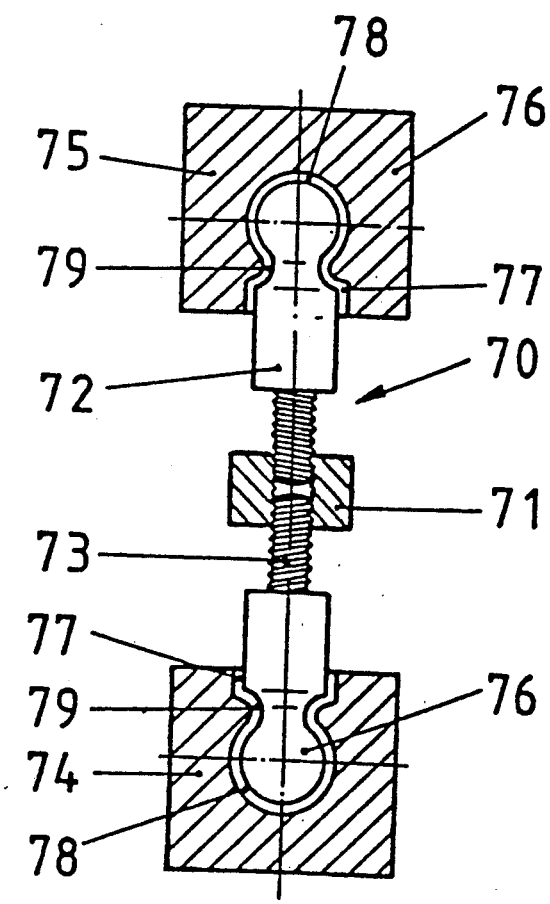

FIG. 16 depicts another embodiment 70 of an adjusting element 25. This embodiment 70 consists of the two threaded spindles 72 and 73 and a sleeve 71 with two counter-threaded sections, each of which engages with one of the spindles. The sleeve 71 is cross-sectionally prismatic in configuration. The free end sections of the threaded spindles are rotatably mounted in abutments 74 and 75, with which they engage in keeping with the principle of a snap union. The abutments are cemented or cast in the row of teeth or its track and the corrected individual plate. The abutments have a bore section 77 opening to their outer surface and merging inwardly into a ball socket 78 for receiving the end sections 76 of the spindles which are shaped as spherical heads. The bore sections center the smooth shafts of the spindle sections, so that adjustment is possible only in the axial direction. In the vicinity of the spherical heads, the end sections have a constriction into which a complementary bead 79 on the abutments snaps during engagement.

Figure 17A:
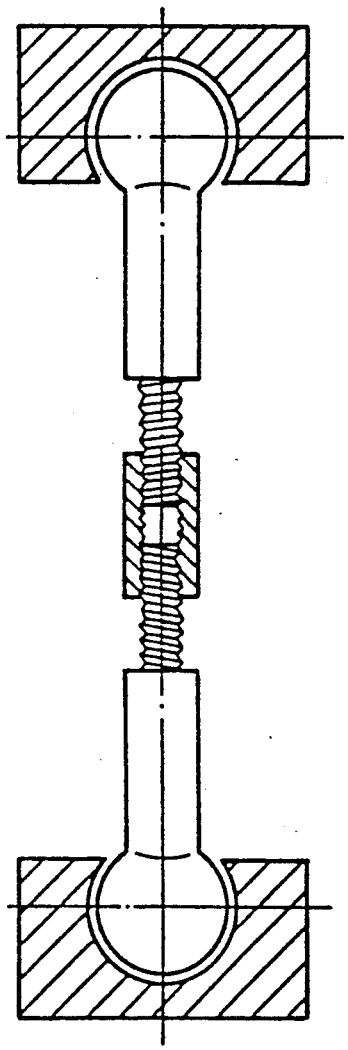
Figure 17B:
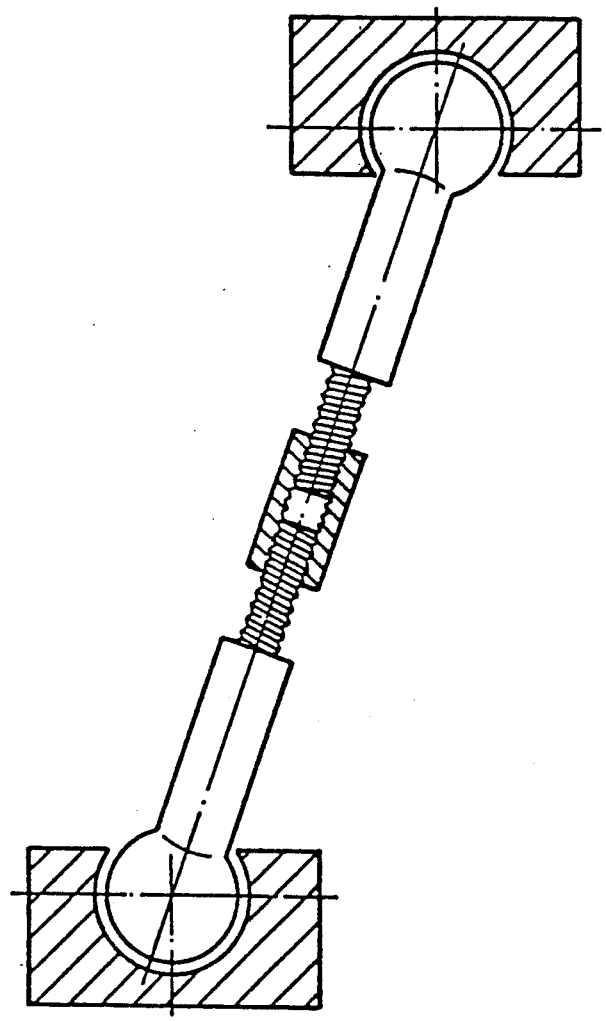

The adjusting element illustrated in FIGS. 17A and 17B differs from that depicted in FIG. 16 in that the abutments are designed as sockets for the spherical heads to permit pivoting of both the spindles and the sleeve in relation to the abutments in keeping with the principle of a ball-and-socket joint. By a frictional seating of the spherical heads in the abutments, assurance is given that adjustments made inside the patient's mouth will be retained.

Figure 18A:
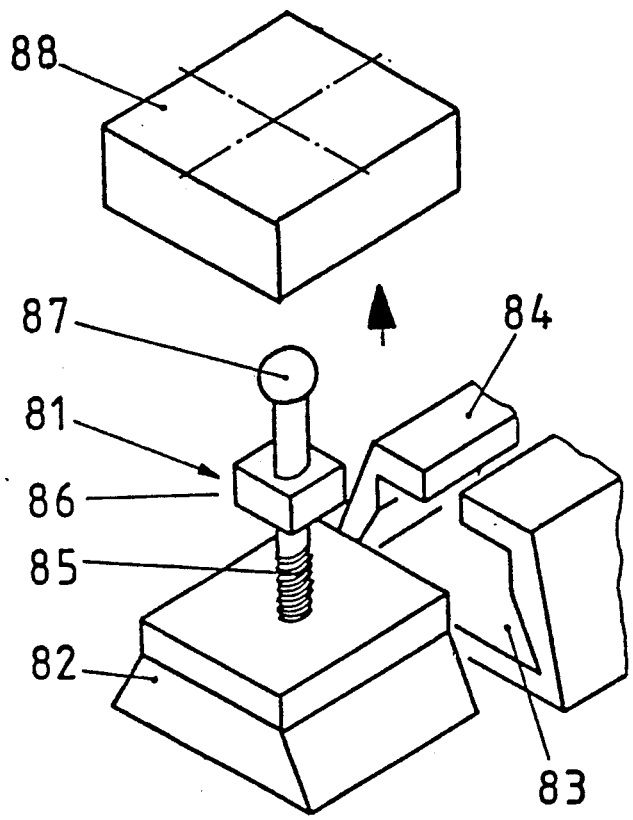
Figure 18B:
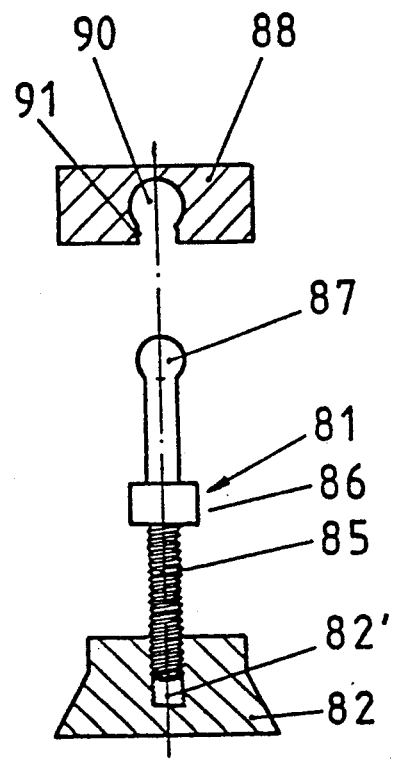

FIGS. 18A and 18B depict a further embodiment of adjusting elements which are used whenever the row of teeth and/or the corrected individual plate has a profile track for the adjusting elements, such as that illustrated in FIGS. 6A and 6B and elsewhere, in which the adjusting elements are displaceable and arrestable.

As shown, an adjusting element 81 has a sliding block 82, which engages in a complementary groove 83 in a profile track 84 illustrated in the accompanying cutout.

The sliding block 82 has a blind bore 82' with internal threading, into which a threaded section 85 of a spindle 86 fits. The spindle has a cross-sectionally square shaft which facilitates its rotation with a suitable spanner. Above the shaft section, the spindle has a spherical head 87 which engages with an abutment 88 in the manner of a snap union.

FIG. 18B is a cross section through the adjusting element 81 which illustrates a socket 90 in the abutment 88 for receiving the spherical head 87 and a bore section 91 leading to its surface.

Figure 18C:
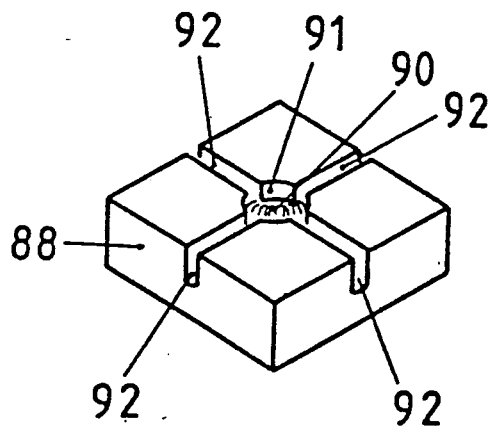

FIG. 18C is a perspective drawing of the abutment 88, which shows four grooves 92, the depths of which are approximately equal to half the thickness of the abutment, ensuring the security of the snap union of the spindle with the abutment.

Figure 19:
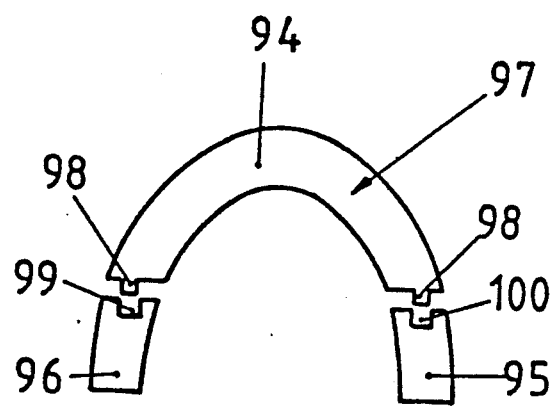
FIG. 19 is an example of an alternate embodiment of a row of teeth with several sections.

Depicted in FIG. 19 is a view of the underside of a row of teeth 97 having three sections 94, 95, and 96. The one section 94 has studs 98 with corrugations on both sides which fit into blind bores 99 and 100 with correspondingly corrugated walls in the sections 95 and 96.

With this invention, the complications prevailing heretofore in the fabrication of dentures are avoided, while the patient, until such time as his final dentures are available, is provided with temporary dentures with characteristics identical to those of the final dentures.

Also within the framework of the invention is the fact that the temporary dentures can be so masked that the separation between the row of false teeth and the corrected individual plate is hidden. To this extent, the term dentures also includes, within the frame of reference of the invention, temporary dentures provided with such masking, so that in many instances it is not necessary, in the sense of the invention, to use the adjusted and arrested temporary plates as described above for the molding of final dentures.

I claim:

1. A temporary denture for at least one jaw of a patient comprising:
   a corrected plate for said at least one jaw;
   a row of false teeth associated with said corrected plate, said row of false teeth extending uninterrupted for the entire length of said at least one jaw, said row of false teeth comprising a plurality false teeth, each of said false teeth being rigidly connected with at least an adjacent one of said false teeth; and
   incompressible, axially adjustable means for adjustably connecting as a singular unit said row of false teeth to said corrected plate to form said temporary denture.

2. The temporary denture of claim 1, wherein said incompressible axially adjustable means for adjustably connecting comprises a plurality of adjustment elements adjustably connecting said corrected plate to said row of false teeth, said adjustment elements being positively engaged with said corrected plate and said row of false teeth.

3. The temporary denture of claim 1, wherein said incompressible, axially adjustable means for adjustably connecting comprises a plurality of adjustment elements adjustably connecting said corrected plate and said row of false teeth, said plurality of adjustment elements adjustably engaged with said row of false teeth and said corrected plate.

4. The temporary denture of claim 1, wherein said row of false teeth comprises a prefabricated strip of plastic material having imprinted teeth.

5. The temporary denture of claim 4, wherein said prefabricated strip of plastic material comprises three consecutive hinged sections.

6. The temporary denture of claim 1, wherein said row of false teeth comprises a shaped track and a plurality of individual false teeth connected to said shaped track.

7. The temporary denture of claim 6, wherein said incompressible, axially adjustable means for adjustably connecting comprises a plurality of adjustable elements which adjustably connect said shaped track to said corrected plate.

8. The temporary denture of claim 1, wherein said incompressible, axially adjustable means for adjustably connecting comprises a plurality of adjustable elements, each adjustable element having one end connected to said row of false teeth at a predetermined location and a connector element provided at its opposite end wherein said corrected plate has a slot in which each said connector element is slidably received to attach said row of false teeth to said corrected plate.

9. The temporary denture of claim 8 wherein said incompressible, axially adjustable connector element is a dovetail element and said slot is a dovetailed slot.

10. The temporary denture of claim 1, wherein said row of false teeth has a plurality of threaded bores threaded in a first direction and said corrected plate has a plurality of threaded bores threaded in a direction opposite said first direction, each threaded bore of said corrected plate being aligned with a respective one of said threaded bores provided in said row of false teeth and wherein said incompressible, axially adjustable means for adjustably connecting is a plurality of bolts, each bolt of said plurality of bolts having a spindle section at each of its opposite ends and a cross-sectionally prismatic shaft intermediate said spindle sections, each spindle section being threaded in an opposite direction, one of said spindle sections of each of said bolts being threadably received in a respective one of said threaded bores provided in said row of false teeth and the other of said spindle sections being threadably received in said threaded bore provided in said corrected plate which is aligned with said threaded bore provided in said row of false teeth in which said one spindle section of said threaded bolt is received.

11. The temporary denture of claim 1, wherein said compressible, axially adjustable means for adjustably connecting comprises a plurality of adjusting elements, each adjusting element having a grub screw portion provided at each end and an intermediate shaft portion having a prismatic cross section, said grub screw portion provided at each end of each adjusting element being threaded in opposite directions, one of said grub screw portions of each adjusting element being threaded into said corrected plate and the other grub screw portion being threaded into said row of false teeth.

12. The temporary denture of claim 1, wherein said compressible, axially adjustable means for adjustably connecting comprises a plurality of attachment members, each attachment member comprising a pair of spindles and a sleeve connecting said pair of spindles, each spindle having a threaded portion and a spherical head, the threaded portions of said pair of spindles being threaded in opposite directions, said sleeve having a prismatic cross section and internal threads provided at each end adapted to threadably receive said threaded portions of said pair of spindles, and wherein said row of false teeth and said corrected plate have abutment members for receiving said spherical heads to connect said row of false teeth to said corrected plate.

13. The temporary denture of claim 12, wherein said abutment members are insertable in said row of false teeth.

14. The temporary denture of claim 13, wherein said abutment members are insertable in said corrected plate.

15. The temporary denture of claim 14, wherein said abutment members are displaceable and arrestably disposed in a track molded in said corrected plate.

16. The temporary denture of claim 14, wherein said abutment members have ball sockets in which said spherical heads are rotatably and pivotably received with sufficient friction to prevent inadvertent displacement of said attachment members.

17. The temporary denture of claim 12, wherein said abutment members are molded in said row of false teeth.

18. The temporary denture of claim 17, wherein said abutment members are molded in said corrected plate.

19. The temporary denture of claim 12, wherein said row of false teeth consists of three hinged sections, said three hinged sections comprising a front-teeth section and two premolar-molar sections, one premolar-molar section being hinged to said front-teeth section on each side thereof, said premolar-molar sections being adjustable and arrestable relative to said front-teeth section.

20. The temporary denture of claim 12, wherein said row of false teeth comprises a front-teeth section and a premolar-molar section connected to each side of said front-teeth section by a ball joint.

21. The temporary denture of claim 12, wherein said row of false teeth comprises a front-teeth section and a premolar-molar section disposed on each side of said front-teeth section, a profile track connecting said premolar-molar sections to said front-teeth section and a flexible threaded spindle rotatably mounted in said front-teeth section for adjusting and arresting the position of said premolar-molar sections relative to said front-teeth section.

22. The temporary denture of claim 12, wherein said row of false teeth comprises a front-teeth section, a premolar-molar section disposed on each side of said front-teeth section and plug and socket connectors having one part thereof formed in said front-teeth section and the other part thereof formed in each of said premolar-molar sections for connecting and arresting said premolar-molar sections to said front-teeth section.

23. The temporary denture of claim 1 wherein said means for adjustably connecting comprises a plurality of adjustable elements, each adjustable element having one end connected to said row of false teeth at a predetermined location and a connector element provided at its opposite end, and wherein said corrected plate has a shaped track in which said connector elements are slidably and arrestably received to adjustably attach said row of false teeth to said corrected plate.

24. A process for fabricating a denture for at least one jaw of a patient in which a first impression of said at least one jaw is made, a first model of said at least one jaw is made from said first impression, a first individual plate for said at least one jaw is made from said first model, and said first individual plate is corrected in the oral cavity of said patient to form a corrected plate, said process characterized by the steps of:
adjustably attaching a row of teeth to said corrected plate by means of a plurality of adjustment elements to produce a temporary denture in which the position of said row of teeth is adjustable relative to said corrected plate;
fitting said temporary denture on said at least one jaw of said patient;
actuating said plurality of adjustment elements when said temporary denture is fitted on said at least one jaw to adjust the position of said row of teeth relative to said corrected plate until said row of teeth is properly positioned in the oral cavity of said patient;
casting a mold for a final denture using said temporary denture after said row of teeth is adjusted to a final position; and
molding said denture using the mold cast from said temporary denture.

25. A process for the fabrication of temporary dentures for an upper jaw and a lower jaw of a patient in which a first impression of said upper jaw and a second impression of said lower jaw are made, models of said upper jaw and said lower jaw are prepared from said first and second impressions, respectively, said models of said upper and lower jaws are fitted together on an articulator, an upper plate for said upper jaw and a lower plate for said lower jaw are prepared from said models, and said upper plate and said lower plate are corrected in the oral cavity of said patient to generate a corrected upper plate and a corrected lower plate, said process for fabrication of temporary dentures comprising the steps of:
adjustably attaching a first row of teeth to said corrected upper plate by means of incompressible, axially adjustable elements;
adjustably attaching a second row of teeth to said corrected lower plate by means of incompressible, axially adjustable elements; and
as a unit, actuating said adjustable elements to shape and adjust the position said first and second rows of teeth relative to said corrected upper and lower plates to form said temporary dentures.

26. A process for fabricating a denture for the upper and lower jaws of a patient, in which a first impression is made of said upper jaw and a second impression is made of said lower jaw, models of said upper and lower jaws are made from said first and second impressions, respectively, said models of said upper and lower jaws are fitted together on an articulator, upper and lower plates are prepared from said models of said upper and lower jaw, respectively, and said upper and lower jaws are corrected in the oral cavity of said patient to generate corrected upper and lower plates, said process for the fabrication of dentures comprising the steps of:
placing a physiognomy arch on the head of said patient, said physiognomy arch having a first row of false teeth matched to said upper jaw of said patient and a second row of false teeth matched to said lower jaw of said patient;
adjusting said first and second row of false teeth to a reference plane;
shaping in an articulator said adjusted first and second rows of false teeth while maintaining the position of said first and second rows of false teeth relative to said reference plane;
fabricating an upper plate for said upper jaw and a lower plate for said lower jaw from said models of said upper and lower jaws, respectively;
correcting said upper and lower plates in the oral cavity of said patient to properly mate with said upper and lower jaws, respectively, to generate corrected upper and lower plates;

adjustably attaching said first and second rows of false teeth to said corrected upper and lower plates, respectively, using a plurality of adjustment elements to form temporary upper and lower dentures;

fitting said temporary upper and lower dentures on said upper and lower jaws of said patient;

actuating said adjustment elements with said temporary upper and lower dentures fitted on said upper and lower jaws, respectively, to finally adjust the position of said first and second row of false teeth relative to said corrected upper and lower plates;

casting final denture molds of said temporary upper and lower dentures; and molding dentures for said upper and lower dentures from said final denture molds.

27. The process of claim 26, wherein said first and second impressions are affixed to said physiognomy arch and adjusted to said reference plane.

28. A process for the fabrication of temporary dentures for an upper and lower jaw of a patient in which a first impression of said upper jaw and a second impression of said lower jaw are made, models of said upper and lower jaws are made from said first and second impressions, said models of said upper and lower jaws are fitted together on an articulator, an upper plate is prepared from said model of said upper jaw and a lower plate is prepared from said model of said lower jaw, and said upper and lower plates are corrected in the oral cavity of said patient to generate corrected upper and lower plates, said process comprising the steps of:

placing a physiognomy arch on the head of said patient, said physiognomy arch having a first row of connected false teeth matched to said upper jaw and a second row of connected false teeth matched to said lower jaw;

adjusting said first and second rows of connected false teeth to a reference plane;

placing said adjusted first and second rows of connected false teeth in an articulator maintaining their adjusted positions;

shaping said adjusted first and second rows of connected false teeth in said articulator;

attaching said first and second rows of connected false teeth to said corrected upper and lower plates using incompressible, axially ajustable elements to form temporary dentures for said upper and lower jaws, respectively; and as a unit, actuating said incompressible, axially adjustable elements to properly fit said first and second rows of connected false teeth relative to said corrected upper and lower plates, respectively.

29. The process according to claim 28, wherein said first and second impressions are affixed to said physiognomy arch and adjusted to said reference plane.

30. A process for the fabrication of an implant-secured denture for at least one jaw of a patient in which a first impression of said at least one jaw is made, a model of said at least one jaw is prepared from said first impression, and said model is fitted on an articulator, said process comprising the steps of:

placing a physiognomy arch having at least one row of false teeth on the head of said patient;

adjusting said at least one row of false teeth to a reference plane;

transferring said at least one row of false teeth to an articulator retaining said adjustment to said reference plane;

shaping said at least one row of false teeth on said articulator to fit on the model of said at least one jaw;

preparing an individual plate from said model of said at least one jaw;

attaching said at least one row of false teeth to said individual plate by means of incompressible, axially adjustable elements; and actuating said incompressible, axially adjustable elements to adjust the position of said at least one row of false teeth as a unit to a final position.

* * * * *